United States Patent [19]

Frank et al.

[11] Patent Number: 5,925,180

[45] Date of Patent: Jul. 20, 1999

[54] ZRO₂-CONTAINING GLASS-CERAMIC

[75] Inventors: Martin Frank, Schaan; Volker Rheinberger, Vaduz; Wolfram Hoeland, Schaan, all of Liechtenstein

[73] Assignee: Ivoclar AG, Liechtenstein

[21] Appl. No.: 08/922,704

[22] Filed: Sep. 3, 1997

Related U.S. Application Data

[62] Division of application No. 08/496,936, Jun. 30, 1995, Pat. No. 5,698,482.

[30] Foreign Application Priority Data

Jul. 1, 1994 [DE] Germany .......................... 442 37 944

[51] Int. Cl.⁶ ............................. C03B 32/00; C03C 10/02
[52] U.S. Cl. ................... 106/35; 433/202.1; 433/212.1; 433/175; 501/5; 501/6; 501/10; 501/32; 501/63; 501/103; 501/104
[58] Field of Search ............................... 501/5, 6, 10, 32, 501/63, 103, 104; 106/35; 433/202.1, 212.1, 175

[56] References Cited

U.S. PATENT DOCUMENTS

| | | | |
|---|---|---|---|
| 3,804,608 | 4/1974 | Gaskell et al. | 501/10 |
| 4,560,666 | 12/1985 | Yoshida et al. | 501/5 |
| 4,587,224 | 5/1986 | Keefer et al. | 501/4 |
| 4,960,733 | 10/1990 | Kasuga et al. | 501/32 |
| 5,034,353 | 7/1991 | Shibuya et al. | 501/3 |
| 5,232,878 | 8/1993 | Kasuga et al. | 501/10 |
| 5,432,130 | 7/1995 | Rheinberger et al. | 501/32 |

FOREIGN PATENT DOCUMENTS

| | | |
|---|---|---|
| 40 20 893 | 1/1991 | Germany . |
| 0 518 454 | 12/1992 | Germany . |
| 62-72539 | 4/1987 | Japan . |

OTHER PUBLICATIONS

Translation of JP 62–72539 Apr. 3, 1987.

Chemical Abstracts, vol. 107, No. 18 Nov. 1987, Abstract No. 160108.

*Primary Examiner*—Melissa Koslow
*Attorney, Agent, or Firm*—Nixon, Hargrave, Devans & Doyle LLP

[57] ABSTRACT

A $ZrO_2$-containing glass ceramic is described, the main crystalline phase of which is formed by $ZrO_2$ and which has at least one further crystalline phase, and which can be used in particular in dentistry.

4 Claims, No Drawings

ZRO$_2$-CONTAINING GLASS-CERAMIC

This is a division of application Ser. No. 08/496,936 filed on Jun. 30, 1995, now U.S. Pat. No. 5,698,482.

The invention relates to a ZrO$_2$-containing glass-ceramic which is suitable in particular for use in dentistry because of its excellent mechanical properties and its processability at low temperatures.

ZrO$_2$-containing glass-ceramics are known. ZrO$_2$ is used in low concentrations of up to 5% by wt. in traditional glass-ceramics as nucleating agents. Glass-ceramics containing up to 15% by wt. ZrO$_2$ are also described in the prior art. However, they contain no phosphorus pentoxide and no or only very small quantities of lithium oxide.

Thus, described for example in U.S. Pat. No. 4,687,749 are glass-ceramics with enstatite as the main crystalline phase which can have a ZrO$_2$ content of up to 15% by wt. The glass-ceramics are free from phosphorus oxide and can contain only small quantities of lithium oxide, namely up to 2% by wt. Further, the materials are very difficult to melt, with the result that high temperatures of more than 1200° C. and in particular of approximately 1500° C. are required to process them.

Known from DE-OS 42 07 180 are ZrO$_2$-containing glass-ceramics which are suitable for preparing tooth crowns, but have no phosphorus oxide or lithium oxide whatsoever. The ZrO$_2$ content is limited to a maximum of 15% by wt., since it is otherwise difficult to obtain a homogeneous glass.

In addition to ZrO$_2$-containing glass-ceramics, which contain ZrO$_2$ homogeneously dissolved in vitreous state in the starting glass and in which ZrO$_2$ crystals subsequently crystallize through thermal treatment of the starting glass, sinter products or sintered bodies with ZrO$_2$ are also known. In the case of these sintered products, crystalline ZrO$_2$ in powder form is mixed to a glass powder and products are obtained by a sintering reaction.

Thus, known for example from DE-PS 39 05 895 are cordierite sintered articles having up to 50% by wt. ZrO$_2$ but which do not contain any phosphorus oxide or lithium oxide whatsoever. The ZrO$_2$ is not obtained by controlled crystallization of an appropriate starting glass but added in powder form. By sintering the ZrO$_2$ powder with powdered starting glass the desired cordierite-ZrO$_2$ sintered products are produced. It is a disadvantage of the described products that they cannot be further processed below 1200° C. by the viscous flow process which is advantageous in dentistry.

It is therefore the object of the invention to provide glass-ceramics with a high ZrO$_2$ content which possess a very good mechanical strength, can be processed at low temperatures of less than 1200° C., can be moulded in particular by pressing, and form a very good adhesive bond with sintered ZrO$_2$ ceramics and accordingly can be used in advantageous manner as materials for moulded dental products.

This object is achieved by the ZrO$_2$-containing glass-ceramic according to the present invention. The invention also relates to a process for the preparation of the glass-ceramic, to its use, and to molded dental products which contain the glass-ceramic.

The ZrO$_2$-containing glass-ceramic according to the invention comprises the following components:

| Component | % by wt. |
|---|---|
| SiO$_2$ | 42.5 to 58.5 |
| Al$_2$O$_3$ | 0 to 7.0 |
| La$_2$O$_3$ | 0 to 9.5 |
| Li$_2$O | 7.0 to 14.5 |
| Na$_2$O | 0 to 7.5 |
| K$_2$O | 0 to 13.5 |
| P$_2$O$_5$ | 4.0 to 13.5 |
| ZrO$_2$ | 15.0 to 28.0 |
| TiO$_2$ | 0 to 6.0 |
| F | 0 to 2.0 |
| BaO | 0 to 6.5 |
| CaO | 0 to 6.0 |
| B$_2$O$_3$ | 0 to 3.3 |
| CeO$_2$ | 0 to 3.0 | and further comprises a ZrO$_2$ crystalline phase and at least one other crystalline phase. The glass-ceramic preferably consists essentially of the given components.

There are particularly preferred quantity ranges for some of the components, and these can be chosen independently of one another and are as follows:

| | |
|---|---|
| SiO$_2$ | 47 [–] to 55% by wt. |
| Al$_2$O$_3$ | 0 [–] to 5% by wt. |
| Li$_2$O | 7 [–] to 14% by wt. |
| Na$_2$O | 0 [–] to 6% by wt. |
| K$_2$O | 0 [–] to 8% by wt. |
| P$_2$O$_5$ | 5 [–] to 11% by wt. |
| ZrO$_2$ | 16 [–] to 25% by wt. |
| F | 0 [–] to 1.5% by wt. |

The procedure for preparing the glass-ceramic according to the invention is that a starting glass which contains the required components is firstly prepared in conventional manner. For this, suitable starting materials, e.g. oxides, oxyhydroxides, carbonates and/or phosphates, are usually melted at temperatures of 1550 to 1600° C. until a homogeneous glass melt is obtained.

The prepared starting glass is then subjected to a heat treatment, as a result of which a controlled crystallization is brought about and consequently the glass-ceramic is formed. There are several possibilities for carrying out the heat treatment and any possible preceding moulding step.

The molten starting glass can for example be firstly cast to give a desired moulded article which is then subjected to the heat treatment by heating to a temperature in the range from 580–1100° C. for 0.5 to 2 hours.

It is also possible that a desired moulded article is formed (a) either by casting molten starting glass or (b) by uniaxial or isostatic cold-pressing and subsequent sintering of granulated starting glass, and compressing this in the viscous state at a temperature of 850–1200° C. The crystallization of the starting glass is effected.

(1) by the sintering of the starting glass,
(2) by the hot-pressing at 850–1200° C. and/or
(3) by a further heat treatment, carried out if necessary after the hot-pressing.

The possibility given here of the heat treatment by hot-pressing illustrates at the same time the particular advantageousness of the glass-ceramic according to the invention compared with traditional high-strength glass-ceramic materials which cannot be compressed at such low temperatures to give moulded articles. Compressing in the viscous state is preferably carried out using the process and pressing oven described in EP-A-0 231 773.

In a preferred embodiment, a further heat treatment can, as already mentioned, be carried out in the temperature range from 580–1100° C. after the heat treatment by pressing in the viscous state.

It has been shown that when the proportion of $ZrO_2$ in the starting glass is increased to more than 28% by wt. a homogeneous glass melt can no longer be obtained. The solubility limit for the glass system used according to the invention obviously lies in this range. For example, when 33% by wt. $ZrO_2$ was used, undissolved $ZrO_2$ was still present after melting. In such a case the glass-ceramics according to the invention, which are obtained by controlled devitrification of a homogeneous starting glass with formation of $ZrO_2$ crystals distributed in highly disperse manner, cannot be achieved.

The glass-ceramics according to the invention were analyzed in more detail by means of scanning electron microscope investigations. It was shown that these are distinguished by a characteristic structure of differently sized crystals. The crystals typically have an average size of 20 $\mu$m relative to the number of crystals. However, crystal sizes of less than or equal to 5 $\mu$m, in particular less than or equal to 1 $\mu$m, are preferred. It is possible that there are still present between these crystals finely crystalline particles less than approximately 400 nm in size which almost touch one another or are in direct contact with one another.

From the results of X-ray diffraction tests and material contrast investigations in the scanning electron microscope, it is concluded that the larger crystals are a $SiO_2$ modification, in particular cristobalite, and/or lithium phosphate. The smaller crystals are $ZrO_2$ crystals, in particular as baddeleyite and/or in tetragonal form, which preferably form the main crystalline phase, and lithium silicate crystals ($Li_2SiO_3$). In some cases, aluminum phosphate ($AlPO_4$), lithium aluminum silicate and, in a low concentration, even lithium zirconium silicate ($Li_2ZrSi_6O_{15}$) are also present.

The $ZrO_2$ crystalline phase preferably contains $ZrO_2$ in tetragonal form. The tetragonal modification of the $ZrO_2$ crystals is preferred, because through it a change to the monoclinic modification can take place upon exposure to an external force, e.g. crack growth. The modification change leads to the known effect of inhibition of crack propagation and therefore to the increase in strength and fracture toughness.

The structure outlined above is typical for the glass-ceramics according to the invention, irrespective of whether they are present as cast or compressed glass-ceramics. Differences only arise as regards the volume proportion of the individual crystalline phases and the size of the crystallites in the individual phases. It is assumed that the individual crystalline phases lead to the increase in the strength of the glass ceramics according to the invention as a result of a dispersion-strengthening effect. The way in which this exactly takes place is still unclear at the present time. In this connection it is also to be considered surprising that the incorporation of cristobalite brings about no negative influence on the strength despite the known differences in the expansion coefficients of its modifications.

Because of their special chemical composition and their special structure the glass-ceramics according to the invention have several advantages which make them particularly suitable as dental materials. Firstly, they have very high flexural strengths of up to 400 MPa. They also show a good temperature change resistance and can be obtained either with a high degree of whiteness, as a result of the high content of $ZrO_2$ crystals, or in translucent form, which is of particular significance for dental materials and the moulded dental products prepared from them. Colouring the glass-ceramics according to the invention is however also possible. This can be carried out a) by colouring the starting glass by adding oxides of the 3-d elements and/or of the 4-f elements and/or by metal colloids or b) by adding colour pigments to the starting glass granulate. It is likewise possible to add fluorescent agents. The glass-ceramics can also contain other usual additives, provided they do not hinder crystallization of the starting glass.

The glass-ceramics according to the invention can also be processed at temperatures below 1200° C., for which purpose in particular the hot-pressing process in the viscous state, which is advantageous for the preparation of dental products, is used. A moulding of conventional high-strength glass-ceramic materials is frequently not possible at these low temperatures. It is also a particular advantage that, in contrast to conventional glass ceramics, the glass-ceramics according to the invention do not react either with the investment material, which is used in the preparation of moulded dental products employing hot-pressing processes. This is an essential advantage for the dental technician processing them.

Finally, the glass-ceramics according to the invention adhere very well to the high-strength pure $ZrO_2$ ceramics, which is important particularly for use in dentistry. Thus, for example, a suitable $ZrO_2$ glass-ceramic can be pressed against a high-strength $ZrO_2$ ceramic post directly following individual moulding, i.e. depending on the cavity in question. The $ZrO_2$ ceramic post is thus anchored firmly in the tooth and further tooth construction can be undertaken.

In view of the properties explained above, the glass-ceramic according to the invention is also preferably used as (a) a dental material or dental product moulded therefrom or as (b) a constituent of a dental material or of a dental product moulded therefrom. Preferred dental products are tooth root structures, in particular posts and cores.

The invention is explained in more detail below with reference to examples.

EXAMPLES

Examples 1 to 18

A total of 18 different glass-ceramics according to the invention were prepared. They had the chemical compositions given in Table I.

In addition to indications of the preparation process selected in each case, details of various properties are given in Table II for some of these glass-ceramics. The values given for the flexural strength are average values from several measurements according to ISO 6872-1984, and the measured values deviate by a maximum of ±30 to 40 MPa from these average values. It is pointed out that in many cases, in addition to the crystalline phases given in the table, yet further crystalline phases formed in a sometimes low concentration and size, but it was not however possible to identify them unequivocally by radiographic means.

Nos. 1 and 6 are examples of cast glass-ceramics and these were prepared according to the process described in Example 19, the heat treatment used in each case being indicated in Table II.

Examples of compressed glass-ceramics are nos. 3, 7, 10 and 11, and these were obtained according to the process described in Example 20. Glass-ceramics nos. 3, 7, 10 and 11 were prepared according to variant A (casting, fine cooling, compressing in the viscous state) and glass ceramic no. 3 also according to variant B (fritting, cold-pressing, sintering, compressing in the viscous state). If after compressing in the viscous state, a further heat treatment was carried out, then this is indicated in the table as "thermal post-treatment".

The examples illustrate how glass-ceramics with different structures and properties can be obtained by changing the chemical composition of the starting glass and the preparation process.

TABLE I

Compositions of glass ceramics according to the invention: (Data in % by wt.)

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| $SiO_2$ | 52.8 | 44.2 | 50.8 | 45.2 | 42.6 | 51.0 | 52.2 | 51.5 | 53.6 | 46.3 | 49.4 | 50.7 | 58.2 | 52.2 | 47.0 | 49.7 | 52.0 | 47.8 |
| $Al_2O_3$ | 3.0 | 3.7 | 2.9 | 6.7 | 3.6 | 2.3 | 3.0 | 3.0 | 1.2 | 3.2 | 2.8 | — | 1.3 | 3.0 | 2.8 | 3.0 | 1.2 | 2.8 |
| $La_2O_3$ | — | 4.5 | — | 2.3 | 4.4 | — | — | — | — | — | — | — | — | — | 9.5 | — | — | — |
| $Li_2O$ | 12.9 | 11.1 | 8.3 | 11.4 | 10.8 | 12.4 | 10.0 | 9.9 | 13.1 | 7.3 | 8.9 | 9.2 | 14.2 | 9.2 | 11.8 | 12.8 | 13.2 | 8.3 |
| $Na_2O$ | — | — | 2.7 | — | — | — | 2.9 | 2.9 | — | — | — | — | — | 7.2 | — | — | — | 3.1 |
| $K_2O$ | — | 2.6 | 4.3 | 2.7 | 2.5 | — | — | — | — | 13.3 | 9.7 | 10.0 | — | — | — | — | — | 4.0 |
| CaO | — | — | — | — | — | — | — | — | — | — | — | — | — | — | — | — | 6.0 | — |
| BaO | — | 6.3 | — | — | 6.1 | — | — | — | — | — | — | — | — | — | — | — | — | — |
| $P_2O_5$ | 10.4 | 12.5 | 10.0 | 13.2 | 12.5 | 8.1 | 10.3 | 10.2 | 4.3 | 11.3 | 9.7 | 10.0 | 4.7 | 7.8 | 9.6 | 10.4 | 4.3 | 10.3 |
| $B_2O_3$ | — | — | — | — | — | — | — | — | — | — | — | — | — | — | — | 3.3 | — | — |
| $ZrO_2$ | 20.9 | 15.1 | 20.1 | 18.5 | 17.5 | 20.2 | 20.7 | 20.5 | 27.8 | 18.6 | 19.5 | 20.1 | 21.6 | 20.6 | 19.3 | 20.8 | 21.3 | 19.7 |
| $TiO_2$ | — | — | — | — | — | 6.0 | — | — | — | — | — | — | — | — | — | — | 2.0 | — |
| F | — | — | 0.9 | — | — | — | 0.9 | 2.0 | — | — | — | — | — | — | — | — | — | 1.0 |
| $CeO_2$ | — | — | — | — | — | — | — | — | — | — | — | — | — | — | — | — | — | 3.0 |

TABLE II

| Example No. | Specimen preparation and heat treatment | Appearance, optical behaviour | Crystalline phases forming in the structure | 3-point flexural strength [MPa] |
|---|---|---|---|---|
| 1 Cast glass ceramic | Bulk glass block: | whitish translucent | Crystalline phases (>300 nm): | 357 |
| Starting glass: cast, bulk | 850° C./0.05 h | | $ZrO_2$: (tetragonal and baddeleyite) $SiO_2$: (cristobalite) Lithium phosphate | |
| 1 Cast glass ceramic | Bulk glass block: | white | $ZrO_2$: tetragonal (<200 nm) | 404 |
| Starting glass: cast, bulk | 950° C./1 h | | Lithium phosphate (<400 nm) $SiO_2$: (cristobalite) <1.5 μm | |
| 3 Pressed glass ceramic | Bulk glass ingot: | white | Lithium phosphate <5 μm | 305 |
| Starting glass: cast, bulk | Compressed in the viscous state at 1050° C.: 10' holding time/5' pressing time | | $ZrO_2$ <500 nm | |
| 3 Pressed glass ceramic | Sintered glass ceramic ingot: | white | Lithium phosphate <5 μm | 180 |
| Starting glass: Powder <90 μm | Compressed in the viscous state at 1050° C.: 10' holding time/5' pressing time | | $ZrO_2$ <1 μm Baddeleyite <20 μm | |
| 6 Cast glass ceramic | Bulk glass block: | white | $ZrO_2$ <200 nm (tetragonal and baddeleyite) $SiO_2$ (cristobalite) <1 μm Lithium phosphate <1 μm | 277 |
| Starting glass: cast, bulk | 900° C./1 h | | | |
| 7 Pressed glass ceramic | Bulk glass ingot | white | Lithium phosphate <5 μm | 250 |
| Starting glass: cast, bulk | Compressed in the viscous state at 1050° C.: 10' holding time/12' pressing time thermal post-treatment at 1000° C. | | $SiO_2$ (cristobalite) <5 μm $ZrO_2$ (<200 nm) | |
| 10 Pressed glass ceramic | Bulk glass ingot | whitish, translucent | Lithium phosphate <500 nm | 199 |
| Starting glass: cast, bulk | Compressed in the viscous state at 1000° C. 5' holding time/32' pressing time thermal post-treatment at 800° C./3 h and 920° C./5 h | | $ZrO_2$ (tetragonal and baddeleyite) <100 nm (possibly $SiO_2$) | |

TABLE II-continued

| Example No. | Specimen preparation and heat treatment | Appearance, optical behaviour | Crystalline phases forming in the structure | 3-point flexural strength [MPa] |
| --- | --- | --- | --- | --- |
| 11 Pressed glass ceramic | Bulk glass ingot | whitish translucent | Lithium phosphate <500 nm | 213 |
| Starting glass: cast, bulk | Compressed in the viscous state at 1000° C.: 5' holding time/25' pressing time thermal post-treatment at 800° C./3 h and 920° C./5 h | | $ZrO_2$: tetragonal and baddeleyite <100 nm (possibly $SiO_2$) | |

Example 19—Cast glass ceramic

Firstly, a starting glass having the chemical composition given in Table I for glass ceramic no. 1 was prepared. For this, an appropriate mixture of oxides, oxyhydroxides, carbonates and phosphates was melted in a platinum/rhodium crucible for 2 hours at temperatures of 1500 to 1600° C. The obtained molten glass was cooled in water, i.e. fritted, dried, granulated and melted again for 2 hours at 1500 to 1600° C. in order to achieve a good homogeneity.

The glass melt was then cast to give a bulk glass block weighing approx. 100 g, and the glass block was cooled from 650° C. so slowly that no stresses formed in the glass. Rods (approx. 5×2×25 mm) were cut out of the glass block and heat-treated at 850° C. for 30 minutes. The flexural strength measured for the obtained glass ceramic rods and other properties of the glass ceramic and details of its structure are listed in Table II.

The glass ceramic prepared in this Example is suitable in excellent manner inter alia because of its high strength, translucence and easy processability and its white appearance as a dental material, which can be used e.g. when preparing a tooth root structure.

Example 20—Compressed glass-ceramics

Firstly, a starting glass having the chemical composition given in Table I for glass-ceramic No. 3 was prepared. For this, a melt of the starting glass was obtained as in Example 19 by melting twice. The obtained melt was then further processed according to two different variants (A) and (B).

Variant (A): Here, the melt of the starting glass was cast to give a bulk glass rod (diameter: 11.3 mm; length: 50 mm) and slowly cooled in order to avoid the formation of stresses. A small cylindrical bulk glass blank (diameter: 11.3 mm; length: 15 mm) was then cut out of the rod and compressed in the viscous state using the pressing process and pressing oven according to EP-A-0 231 773 under vacuum and at a temperature of 1050° C. and at 5 bar pressing pressure to give the desired specimen geometry.

Compared with conventional materials, it is a particular advantage of this glass-ceramic that it can be processed even at temperatures lower than 1200° C., namely at 1050° C., to give individually moulded dental products, e.g. can be pressed against high-strength $ZrO_2$ ceramic posts. Nor does compression lead either to an undesired reaction, which frequently occurs with conventional materials, with the required investment material, which emphasizes the excellent suitability of the glass ceramic according to the invention for the preparation of individually moulded dental products.

Variant (B): Here, the starting glass melt was firstly fritted by pouring it into water, and the resulting frit was ground and sieved to a grain size of less than 90 μm. The obtained glass powder was then compressed using a uniaxial drying press at 1000 bar pressing pressure to give small cylinders. The glass cylinders were then sintered in a vacuum at a temperature of 850° C. for 30 minutes in a furnace, as a result of which devitrification of the starting glass already took place to a certain extent. The obtained ingots were finally compressed under vacuum in the viscous state using the pressing process and pressing oven according to EP-A-0 231 773 to give the desired specimen geometry.

The glass-ceramic according to the invention obtained in this way also displayed the advantages obtained with variant (A) during processing and was thus able to be used in advantageous manner e.g. for the preparation of individually moulded restorations for posts.

We claim:

1. A dental material comprising a $ZrO_2$-containing glass-ceramic composition, comprising a $ZrO_2$ crystalline phase, a lithium phosphate crystalline phase, and at least one additional crystalline phase, and comprising the following components:

| Component | % by wt. | |
| --- | --- | --- |
| $SiO_2$ | 42.5 to | 58.5 |
| $Al_2O_3$ | 0 to | 7.0 |
| $La_2O_3$ | 0 to | 9.5 |
| $Li_2O$ | 7.0 to | 14.5 |
| $Na_2O$ | 0 to | 7.5 |
| $K_2O$ | 0 to | 13.5 |
| $P_2O_5$ | 4.0 to | 13.5 |
| $ZrO_2$ | 15.0 to | 28.0 |
| $TiO_2$ | 0 to | 6.0 |
| F | 0 to | 2.0 |
| BaO | 0 to | 6.5 |
| CaO | 0 to | 6.0 |
| $B_2O_3$ | 0 to | 3.3 |
| $CeO_2$ | 0 to | 3.0. |

2. A tooth root pin comprising a $ZrO_2$-containing glass-ceramic composition, comprising a $ZrO_2$ crystalline phase, a lithium phosphate crystalline phase, and at least one additional crystalline phase, and comprising the following components:

| Component | % by wt. | |
| --- | --- | --- |
| $SiO_2$ | 42.5 to | 58.5 |
| $Al_2O_3$ | 0 to | 7.0 |
| $La_2O_3$ | 0 to | 9.5 |
| $Li_2O$ | 7.0 to | 14.5 |
| $Na_2O$ | 0 to | 7.5 |
| $K_2O$ | 0 to | 13.5 |
| $P_2O_5$ | 4.0 to | 13.5 |
| $ZrO_2$ | 15.0 to | 28.0 |
| $TiO_2$ | 0 to | 6.0 |

-continued

| Component | % by wt. |
|---|---|
| F | 0 to 2.0 |
| BaO | 0 to 6.5 |
| CaO | 0 to 6.0 |
| $B_2O_3$ | 0 to 3.3 |
| $CeO_2$ | 0 to 3.0. |

3. A tooth root restoration comprising a $ZrO_2$-containing glass-ceramic composition, comprising a $ZrO_2$ crystalline phase, a lithium phosphate crystalline phase, and at least one additional crystalline phase, and comprising the following components:

| Component | % by wt. |
|---|---|
| $SiO_2$ | 42.5 to 58.5 |
| $Al_2O_3$ | 0 to 7.0 |
| $La_2O_3$ | 0 to 9.5 |
| $Li_2O$ | 7.0 to 14.5 |
| $Na_2O$ | 0 to 7.5 |
| $K_2O$ | 0 to 13.5 |
| $P_2O_5$ | 4.0 to 13.5 |
| $ZrO_2$ | 15.0 to 28.0 |
| $TiO_2$ | 0 to 6.0 |
| F | 0 to 2.0 |
| BaO | 0 to 6.5 |
| CaO | 0 to 6.0 |
| $B_2O_3$ | 0 to 3.3 |
| $CeO_2$ | 0 to 3.0. |

4. A molded dental product comprising a $ZrO_2$-containing glass-ceramic composition, comprising a $ZrO_2$ crystalline phase, a lithium phosphate crystalline phase, and at least one additional crystalline phase, and comprising the following components:

| Component | % by wt. |
|---|---|
| $SiO_2$ | 42.5 to 58.5 |
| $Al_2O_3$ | 0 to 7.0 |
| $La_2O_3$ | 0 to 9.5 |
| $Li_2O$ | 7.0 to 14.5 |
| $Na_2O$ | 0 to 7.5 |
| $K_2O$ | 0 to 13.5 |
| $P_2O_5$ | 4.0 to 13.5 |
| $ZrO_2$ | 15.0 to 28.0 |
| $TiO_2$ | 0 to 6.0 |
| F | 0 to 2.0 |
| BaO | 0 to 6.5 |
| CaO | 0 to 6.0 |
| $B_2O_3$ | 0 to 3.3 |
| $CeO_2$ | 0 to 3.0. |

* * * * *